United States Patent [19]

Müller et al.

[11] 4,420,429

[45] Dec. 13, 1983

[54] PRODUCTION OF ALKYL ESTERS OF SATURATED ALIPHATIC CARBOXYLIC ACIDS

[75] Inventors: Wolfgang H. E. Müller; Peter Hofmann, both of Marl, Fed. Rep. of Germany

[73] Assignee: Chemische Werke Hüls A.G., Marl, Fed. Rep. of Germany

[21] Appl. No.: 291,952

[22] Filed: Aug. 11, 1981

[30] Foreign Application Priority Data

Sep. 12, 1980 [DE] Fed. Rep. of Germany ....... 3034421

[51] Int. Cl.$^3$ ............................................... C11C 3/02
[52] U.S. Cl. ............................................. 260/410.9 R
[58] Field of Search ................................. 260/410.9 R

[56] References Cited

U.S. PATENT DOCUMENTS 2,076,111  4/1937  Bannister ............... 260/410.9 R X
3,507,891  4/1970  Hearne ..................... 260/410.9 R
3,906,016  9/1975  Isa .............................. 260/410.9 R
4,041,057  8/1977  Fanning ..................... 260/410.9 R

OTHER PUBLICATIONS

Peter Hofmann et al., "Hydrocarboxymethylation–An Attractive Route from Olefins to Fatty Acid Esters?" Sep. 1980, I & EC Product Research & Development, vol. 19, p. 330–334.

Primary Examiner—Helen M. S. Sneed
Attorney, Agent, or Firm—Wells & Wells

[57] ABSTRACT

A process for the production of alkyl esters of saturated aliphatic carboxylic acids made by reacting olefins with carbon monoxide and alkanol in the presence of a catalyst consisting of a cobalt compound and a promoter selected from pyridine, a non-ortho-substituted alkylpyridine or mixtures thereof at elevated pressure and temperature and with feedback of unconverted input materials, the water contained in the reaction mixture being separated as much as possible during the reprocessing from the flows of substances slated for feedback.

10 Claims, No Drawings

PRODUCTION OF ALKYL ESTERS OF SATURATED ALIPHATIC CARBOXYLIC ACIDS

CROSS-REFERENCE TO RELATED APPLICATIONS

Applicants claim priority under 35 USC 119 for application P No. 30 34 421.9, filed Sept. 12, 1980 in the Patent Office of the Federal Republic of Germany.

The disclosure of coinventor Hofmann's copending application Ser. No. 125,482, filed Feb. 28, 1980 is incorporated herein to show alkoxycarbonylation procedures carried out in the presence of cobalt catalysts and a promoter from the group pyridine, non-ortho-substituted alkylpyridine and mixtures thereof.

Also incorporated herein is coinventor Hofmann's copending application Ser. No. 203,393, filed Nov. 3, 1980 to show that olefins with internal double bonds can be produced by dehydrogenation of paraffins or by chlorination followed by dehydrochlorination of paraffins.

BACKGROUND OF THE INVENTION

The field of the invention is the production of alkyl esters of saturated aliphatic carboxylic acids and the present invention is particularly concerned with reacting olefins with carbon monoxide and alkanol in the presence of a catalyst consisting of a cobalt compound and a promoter selected from pyridine, non-ortho-substituted alkylpyridine or mixtures thereof at elevated pressures and elevated temperatures and with feedback of unconverted input materials.

The state of the art of such alkoxycarbonylation reactions may be ascertained by reference to U.S. Pat. Nos. 3,507,891; 3,906,016; and 4,041,057, and the article, "Hydrocarboxymethylation—an Attractive Route from Olefins to Fatty Acid Esters?" by Peter Hofmann et al as published in I & EC, Product Research and Development, Vol. 19, Sept. 1980, pp. 330–334, the disclosures of which are incorporated herein.

It is known to prepare fatty acid esters by reacting olefins with carbon monoxide and a compound having a replaceable hydrogen atom such as an alkanol in the presence of a catalyst containing a metal of Group VIII of the Periodic Table of elements and possibly also a promoter as disclosed by J. Falbe, "Synthesen mit Kohlenmonoxid", Springer publisher, Berlin, Heidelberg, New York (1967).

An especially preferred variation of this reaction, which is termed alkoxycarbonylation, has been found to be the conversion in the presence of a cobalt catalyst. An especially preferred embodiment consists in further adding a promoter, especially pyridine, non-ortho-substituted alkylpyridines and mixtures thereof.

The economy of such a process for making fatty acid esters depends decisively on the ester yield to be achieved. This yield, in the case of, for instance, a procedure for feeding back unconverted input and accessory materials into the alkoxycarbonylation stage as disclosed in U.S. Pat. No. 4,041,057 is degraded by the formation of those by-products which have a higher boiling point than the desired reaction products, these by-products being termed high boiling substances. On account of the formation of these high boiling point substances, there results not only a higher olefin consumption per unit weight of the desired end product, but also losses of other valuable input materials in the course of the necessary separation of these high boiling point substances.

SUMMARY OF THE INVENTION

Having in mind the limitations of the prior art, it is therefore an object of the present invention to create a process wherein the proportion of the high boiling point substances is as low as possible.

This object is achieved according to the present invention in a process for the production of alkyl esters of saturated aliphatic carboxylic acids by reacting olefins with carbon monoxide and alkanol in the presence of a catalyst consisting of a cobalt compound and a promoter selected from pyridine, a non-ortho-substituted alkylpyridine or a mixture thereof at elevated pressures and elevated temperatures and with feedback of the unconverted input materials, where the water contained in the reaction mixture is removed as much as possible during the reprocessing of the reaction mixture from the flow of substances slated for feedback.

By elevated pressures are meant carbon monoxide pressures of about 10 to 800 and preferably 100 to 300 bars. By elevated temperatures are meant temperatures of about 80° to 300° C. and preferably 150° to 220° C.

DESCRIPTION OF THE PREFERRED EMBODIMENTS

The results of the present invention are new and unexpected because in the pertinent state of the art, it is precisely the addition of water which is represented as being the critical or advantageous process step in order to increase the yield in fatty acid esters as disclosed in U.S. Pat. No. 3,906,016 at Column 3, beginning at line 14.

In principle the process of the present invention applies to all the alkoxycarbonylation procedures carried out in the presence of a cobalt catalyst such as disclosed in U.S. Pat. No. 3,507,891 and U.S. patent application Ser. No. 125,482. Thus, most of all, the selection of the olefin used is not critical, that is, both straight-chain and branched alpha-olefins can be used, also olefins with an internal double bond. Moreover, olefins with more than one double bond, and those with substituents, such as aryl, cyano, carboxymethyl and hydroxyl groups also are suitable.

As a rule, olefins having 2 to 40, preferably 4 to 20 C atoms are used, which may be obtained by the methods known to be the state of the art. Thus, alpha-olefins may be obtained by the Ziegler synthesis reaction of ethylene as disclosed in U.S. Pat. No. 3,310,600, or by wax cracking, and olefins with an internal double bond, which preferably are used in the process of the present invention, can be obtained by catalytically dehydrogenating paraffins and then dehydrochlorinating the chloroparaffins as disclosed in British Pat. No. 1,037,868 and U.S. patent application Ser. No. 203,393.

As regards the last mentioned method, use is made as a rule of blends of paraffin, that is, mixtures of different C numbers, so that the olefins obtained also lack any uniform C number.

Moreover, obviously all conceivable isomeric forms are found in these olefin mixtures.

Besides the pure olefins and possibly substituted olefins, it is possible too to make use of those olefins having a paraffin content up to for instance 85%. There is a paraffin content in the olefins because no complete conversion is achieved in the production of olefins and the unconverted paraffins are not separated out or are only incompletely separated.

Not only is the olefin used not critical, but also the kind of alkanol being reacted with the olefin and the carbon monoxide is not critical for the process of the present invention. As a rule, alkanols having 1 to 10, preferably 1 to 4 C atoms are used. Typically representative substances selected from the group of primary alcohols are for instance methanol, ethanol, propanol-(1) and butanol-(1).

Again, it is immaterial which cobalt catalyst compound is used in the alkoxycarbonylation. Cobalt carbonyls, for instance dicobalt octacarbonyl, are just as suitable carboxylic-acid cobalt salts such as cobalt acetate, cobalt naphthenate, and cobalt-2-ethylhexanoate. Salts of cobalt with inorganic acids such as cobalt nitrate and cobalt sulfate are also useful. Preferably those carboxylic acid cobalt salts are used having anions corresponding to the acid group of the fatty acid esters formed in the alkoxycarbonylation.

Applicable promoters are pyridine and all non-ortho-substituted alkylpyridines such as 3-picoline and 4-picoline, 3,4-lutidine and 3,5-lutidine and 3-ethylpyridine and 4-ethylpyridine or mixtures of these.

Lastly, the conditions of the reaction under which the alkoxycarbonylation is carried out are not significant for the process of the present invention. As a rule, the alkoxycarbonylation procedures are carried out at temperatures of about 80 to 300, preferably 150° to 200° C. and at carbon monoxide pressures of about 10 to 800, preferably 100 to 300 bars. Depending on the kind of olefin being converted, the concentration of the cobalt used as catalyst is in a range between about 0.005 and 0.2 gram-atom of cobalt per mole of olefin, the proportion of the pyridine and/or non-ortho-substituted alkylpyridine used as cocatalyst is in the range from about 3 to 100, preferably 5 to 50 moles per gram-atom of cobalt, and the amount of the alkanol used per mole of olefin is in a range between about 1 and 20, preferably 1 and 10 moles.

What is however process-critical for the procedure of the present invention is that there be as extensive a separation as possible of the water contained in the reaction mixture from the flows of substances which are to be fed back into the alkoxycarbonylation stage. As a rule, the water content of the fed back flows of substances should be less than 1, preferably less than 0.5 and especially preferred less than 0.1% by weight referred to the olefin used (fresh olefin plus any feedback olefin).

The removal of the water is implemented by methods such as distillation, azeotropic distillation, treatment by dessicant absorbents such as molecular sieves, sodium sulfate and silica gel or by freezing-out.

The defined invention can be applied both to discontinuous and continuous methods. However, the application is especially advantageous with a continuous process wherein one or more flows of substances (unconverted olefin, alkanol and carbon monoxide as well as recovered catalyst) are being fed back, as disclosed in U.S. Pat. No. 4,041,057.

In general, the process of the present invention is carried out so that the reaction mixture first is separated for instance by distillation into several fractions. The main fractions are always alkanol, olefin, fatty acid ester and cocatalyst. The sump products are the high boiling point substances and a residue containing the cobalt. In this reprocessing mode, the water to be separated is almost exclusively located in the distillate fractions, which ordinarily and obviously, except for the fatty acids being further processed, for instance, into surfactants, are fed back into the alkoxycarbonylation stage. The distillate fractions are previously rid of water as far as possible or necessary by means of one of the methods already described.

The process of the present invention is described in further detail below in relation to the following examples.

EXAMPLE 1

The mixture of the following input substances is used with the molar ratios below 1 mole of n-dodecene (isomeric mixture with an n-dodecene-(1) proportion less or equal to 1% by weight; purity 90% by weight; water content 0.001% by weight)

2 moles of methanol (purity 90% by weight; water content 0.018% by weight)

0.3 moles of gamma-picoline (purity 98% by weight; water content 0.095% by weight)

0.03 gram-atom of cobalt in the form of a residue obtained from the reprocessing by distillation of the alkoxycarbonylation mixtures and containing 8% by weight of cobalt (water content less than 0.0001% by weight) [the contaminations contained in the input substances are by-products from the alkxoycarbonylation reaction that were not separated by the distillation]

and is continuously pumped into an agitated autoclave where it is made to react (=reaction cycle 1) under the following conditions:

temperature of reaction—185° C.

CO hot pressure (CO contains 1% by vol $H_2$)—180 bars dwell time—1.6 hr.

After treatment with air (50 liters of air per liter of reaction mixture) at 40° C. and 1 bar, the reaction mixture is subjected to the following continuous reprocessing:

The entire reaction mixture is decomposed in a falling film evaporator (FFE) into a distillate fraction containing the unconverted methanol (water content of this fraction is 1.45% by weight) and into a methanol-free sump product.

The methanol-free sump product of the falling film evaporator is separated by distillation into gamma-picoline (water content 0.090% by weight), olefin (water content 0.001% by weight) and tridecanoic acid methyl ester collecting as top fractions and into sump products in the form of high boiling point substances and a cobalt residue (water content less than 1 ppm by weight).

Of the substances slated for feedback (methanol, gamma-picoline, olefin and cobalt residue), only the methanol is rid of water by renewed distillation: the head product from this distillation stage is methanol with a water content of 0.021% by weight. The fed back cobalt residue prior to its new application is subjected to a regeneration with synthesis gas (50% by mole of $H_2$, 50% by mole of CO) at 200 bars and 170° C. The remaining substances require no further treatment. However, to prevent an enrichment in the impurities in the fed back flows of substances, 5% of the methanol and 4% of the olefin are taken out. After replenishing the substances consumed by the reaction (in case of methanol and olefin) or those taken out and the losses incurred by secondary reactions or in the case of reprocessing (in case of methanol, olefin, gamma-picoline and cobalt catalyst) by means of water-free fresh substances, the alkoxycarbonylation reaction is again carried out while observing the initially cited quantitative ratios and conditions of reaction.

The relation between the water content of the flows of substances fed back into the reaction (from the previous reaction cycle), the olefin conversion, the amount of the high boiling point substances obtained as by-products and the ester selectivity, is shown in Table 1 for 30 consecutive cycles of reaction.

amount of the high boiling substances obtained as by-products, and also the ester selectivity, in such a procedure, is represented in Table 2 for 10 consecutive reaction cycles.

EXAMPLE 3

Example 1 is repeated except that an olefin (purity 90% by weight; water content 0.02% by weight) is used in the reaction cycle 1, of which the olefin proportion consists of 30% by weight of an isomeric mixture of n-dodecenes and of 70% by weight of n-dodecene-(1)

TABLE 1

| Reaction cycle | Water content (% by weight) | | | | | Water Content[1] (% by weight) | Olefin conver. % | High Boiling Point Substance (% by weight)[2] | Ester Selectivity molar % |
|---|---|---|---|---|---|---|---|---|---|
| | Fed back methanol FFE distillate | Fed back methanol distilled again | Fed back γ-picoline | Fed back Olefin | Cobalt residue | | | | |
| 1 | 3 | 3 | 3 | 3 | 3 | 3 | 60 | 1.2 | 96.8 |
| 2 | 1.45 | 0.021 | 0.090 | 0.001 | <0.0001 | 0.022 | 57 | 1.0 | 97.0 |
| 5 | 1.40 | 0.018 | 0.085 | 0.001 | <0.0001 | 0.021 | 57 | 1.0 | 97.0 |
| 10 | 1.54 | 0.020 | 0.103 | 0.001 | <0.0001 | 0.025 | 63 | 1.4 | 96.6 |
| 20 | 1.55 | 0.022 | 0.110 | 0.002 | <0.0001 | 0.027 | 61 | 1.3 | 96.7 |
| 30 | 1.47 | 0.020 | 0.102 | 0.001 | <0.0001 | 0.025 | 60 | 1.2 | 96.8 |

[1]sum of the water contents in fed back methanol (distilled again), fed back gamma picoline, fed back olefin and cobalt residue, referred to input olefin (= fed back and fresh olefin)
[2]referred to tridecanoic acid methyl ester
[3]water contents of the input substances for the reaction cycle 1, see text of example
FFE = falling film evaporator

EXAMPLE 2

Example 1 is repeated except that the methanol from the air-treated reaction mixture is not separated by a falling film evaporator but by means of a column with 20 theoretical plates filled with Raschig rings. The major amount of the water contained in the reaction mixture in such a procedure does not collect in the methanol fraction, rather in the picoline fraction, and is removed from the latter by molecular sieve treatment.

The relation between the water content of the flows of substances (from the previous reaction cycle) fed back into the reaction, the olefin conversion, the used as in Example 1, and in that the alkoxycarbonylation reaction is carried out at a temperature of 170° C. and a pressure of 270 bars. The olefin consumed by the reaction or lost by the removal or in the course of reprocessing, however, is replaced by water-free n-dodecene-(1).

The relation obtained for such a procedure between the water content of the flows of substances (from the previous reaction cycle) fed back into the reaction, the olefin conversion, the amount of the high boiling point substances obtained as by-products and the ester selectivity is listed in Table 3 for 10 consecutive reaction cycles.

TABLE 2

| Reaction cycle | Water content (% by weight) | | | | | Water Content[1] (% by weight) | Olefin conver. % | High Boiling Point Substance (% by weight)[2] | Ester Selectivity molar % |
|---|---|---|---|---|---|---|---|---|---|
| | Fed back methanol | Fed back γ-picoline distillate | Fed back γ-picoline after molecular sieve treatment | Fed back Olefin | Cobalt residue | | | | |
| 1 | 3 | 3 | 3 | 3 | 3 | 3 | 59 | 1.4 | 96.6 |
| 2 | 0.012 | 2.73 | 0.008 | 0.001 | <0.0001 | 0.005 | 60 | 1.5 | 96.5 |
| 5 | 0.020 | 3.02 | 0.015 | 0.002 | 0.0002 | 0.009 | 62 | 1.3 | 96.6 |
| 10 | 0.014 | 2.70 | 0.010 | 0.001 | <0.0001 | 0.006 | 60 | 1.4 | 96.8 |

[1]sum of the water contents in fed back methanol, fed back gamma picoline (treated with molecular sieve), fed back olefin & cobalt residue, referred to input olefin (= fed back and fresh olefin)
[2]referred to tridecanoic acid methyl ester
[3]water contents of the input substances for the reaction cycle 1, see text of example

TABLE 3

| Reaction cycle | Water content (% by weight) | | | | | Water Content[1] (% by weight) | Olefin conver. % | High Boiling Point Substance (% by weight)[2] | Ester Selectivity molar % |
|---|---|---|---|---|---|---|---|---|---|
| | Fed back methanol FFE distillate | Fed back methanol distilled again | Fed back γ-picoline | Fed back Olefin | Cobalt residue | | | | |
| 1 | 3 | 3 | 3 | 3 | 3 | 3 | 67 | 1.1 | 97.0 |
| 2 | 1.37 | 0.018 | 0.095 | 0.001 | <0.0001 | 0.021 | 67 | 1.0 | 96.8 |
| 5 | 1.45 | 0.021 | 0.090 | 0.001 | <0.0001 | 0.021 | 69 | 0.9 | 97.2 |

TABLE 3-continued

| Reaction cycle | Water content (% by weight) | | | | | Water Content[1] (% by weight) | Olefin conver. % | High Boiling Point Substance (% by weight)[2] | Ester Selectivity molar % |
|---|---|---|---|---|---|---|---|---|---|
| | Fed back methanol FFE distillate | Fed back methanol distilled again | Fed back γ-picoline | Fed back Olefin | Cobalt residue | | | | |
| 10 | 1.42 | 0.021 | 0.092 | 0.001 | <0.0001 | 0.022 | 66 | 1.2 | 96.7 |

[1]sum of the water contents in fed back methanol (distilled again), fed back gamma picoline, fed back olefin and cobalt residue, referred to input olefin, (= fed back and fresh n-dodecene-(1))
[2]referred to tridecanoic acid methyl ester
[3]water contents of the input substances for the reaction cycle 1, see text of example
FFE = falling film evaporator

EXAMPLE 4

Example 1 is repeated, except that
(1) methanol is replaced by the same molar amount of ethanol (purity 90% by weight; water content: 0.01% by weight)
(2) gamma-picoline is replaced by the same molar amount of 4-ethylpyridine (water content 0.06% by weight)
(3) the amount of alkanol removed is reduced to 2% of the ethanol fed back
(4) the amount of olefin removed is decreased to 3% of the olefin fed back
(5) water is separated by azeotropic distillation with benzene as the entraining agent from the aqueous ethanol collecting as the distillate from the falling film evaporator.

The relation obtained in this procedure between the water content of the flows of substance (from the previous reaction) cycle into the reaction, the olefin conversion, the amount of the high boiling point substances obtaining as by-product and the ester selectivity is listed in Table 4 for 10 consecutive reaction cycles.

CONTROL EXAMPLE (COMPARISON TEST)

Example 1 is repeated except that there is no separation of the water from the aqueous methanol obtained as the distillate of the falling film evaporator.

The relation obtaining for such a procedure between the water content of the flows of substances (from the previous reaction cycle) fed back into the reaction, the olefin conversion, the amount of the high boiling point substances collecting as by-product and the ester selectivity is shown in Table 5 for 11 consecutive reaction cycles.

TABLE 4

| Reaction cycle | Water content (% by weight) | | | | | Water Content[1] (% by weight) | Olefin conver. % | High Boiling Point Substance (% by weight)[2] | Ester Selectivity molar % |
|---|---|---|---|---|---|---|---|---|---|
| | Fed back ethanol FFE distillate | Fed back ethanol after azeotropic distillation | Fed back 4-ethyl pyridine | Fed back Olefin | Cobalt residue | | | | |
| 1 | 3 | 3 | 3 | 3 | 3 | 3 | 36 | 0.7 | 97.0 |
| 2 | 1.10 | 0.020 | 0.060 | 0.001 | <0.0001 | 0.022 | 33 | 0.7 | 97.5 |
| 5 | 1.03 | 0.030 | 0.062 | 0.001 | <0.0001 | 0.027 | 35 | 0.6 | 97.2 |
| 10 | 1.10 | 0.023 | 0.064 | 0.001 | <0.0001 | 0.024 | 35 | 0.7 | 96.9 |

[1]sum of the water contents in fed back ethanol (after azeotropic distillation), 4-ethylpyridine, fed back olefin and cobalt residue, referred to input olefin (= fed back and fresh olefin)
[2]referred to tridecanoic acid methyl ester
[3]water contents of the input substances for the reaction cycle 1, see text of example
FFE = falling film evaporator

TABLE 5

| Reaction cycle | Water content (% by weight) | | | | Water Content[1] (% by weight) | Olefin conver. % | High Boiling Point Substance (% by weight)[2] | Ester Selectivity molar % |
|---|---|---|---|---|---|---|---|---|
| | Fed back methanol FFE distillate | Fed back γ-picoline | Fed back Olefin | Cobalt residue | | | | |
| 1 | 3 | 3 | 3 | 3 | 3 | 60 | 1.1 | 97.0 |
| 2 | 1.48 | 0.102 | 0.001 | <0.0001 | 0.43 | 58 | 2.5 | 95.2 |
| 3 | 2.3 | 0.18 | 0.001 | <0.0001 | 0.67 | 60 | 3.2 | 94.7 |
| 5 | 3.7 | 0.30 | 0.001 | <0.0001 | 1.08 | 62 | 4.3 | 93.5 |
| 7 | 4.9 | 0.33 | 0.001 | <0.0001 | 1.42 | 61 | 4.6 | 93.0 |
| 9 | 6.0 | 0.47 | 0.001 | <0.0001 | 1.75 | 61 | 5.0 | 92.2 |
| 11 | 6.6 | 0.49 | 0.001 | <0.0001 | 1.91 | 59 | 4.8 | 92.1 |

[1]sum of the water contents in fed back methanol fed back gamma picoline, fed back olefin and cobalt residue, referred to input olefin (= fed back and fresh olefin)
[2]referred to tridecanoic acid methyl ester
[3]water contents of the input substances for the reaction cycle 1, see text of example
FFE = falling film evaporator

We claim:
1. In a process for preparing an alkylester of a saturated aliphatic carboxylic acid by:
(a) reacting at elevated temperatures and pressure, input material comprising olefin, alkanol and carbon monoxide in the presence of a catalyst consisting of a cobalt compound and a promoter selected from the group consisting of pyridine, non-ortho-substituted alkylpyridine, and mixtures thereof to form a reaction mixture containing water, said alkylester, unreacted olefin, unreacted promoter, catalyst residue, and unreacted alkanol;

(b) separating alkylester from said water, unreacted olefin, unreacted promoter, catalyst residue, and unreacted alkanol;
(c) regenerating said catalyst residue; and
(d) feeding back to step (a) said water, said unreacted olefin, said unreacted promoter, said regenerating catalyst, and said unreacted alkanol, the improvement comprising:
(e) separating water from the groups consisting of said water and said unreacted alkanol or said water and said unreacted promoter.

2. The process of claim 1, wherein said group is said water and said unreacted alkanol.

3. The process of claim 1, wherein said group is said water and said unreacted promoter.

4. The process of claim 2, wherein step (b) is carried out in a falling film evaporator and step (e) is carried out by distillation to separate said water from said alkanol.

5. The process of claim 3, wherein step (b) is carried out in a distillation column and step (e) is carried out by molecular sieve treatment.

6. The process of claim 1, wherein the olefin input material is prepared by chlorinating paraffins and then dehydrochlorinating the chloroparaffins.

7. The process of claim 1, wherein the olefin input material is prepared by catalytically dehydrogenating paraffins.

8. The process of claim 1, wherein said feedback has a water content less than 1% by weight referred to said olefin input material.

9. The process of claim 1, wherein said feedback has a water content less than 0.5% by weight referred to said olefin input material.

10. The process of claim 1, wherein said feedback has a water content less than 0.1% by weight referred to said olefin input material.

* * * * *